US011142701B2

(12) United States Patent
Myllyoja et al.

(10) Patent No.: US 11,142,701 B2
(45) Date of Patent: Oct. 12, 2021

(54) PROCESS FOR THE PRODUCTION OF RENEWABLE BASE OIL, DIESEL AND NAPHTHA

(71) Applicant: Neste Oyj, Espoo (FI)

(72) Inventors: Jukka Myllyoja, Porvoo (FI); Pekka Nurmi, Porvoo (FI); Jaana Kanervo, Porvoo (FI); Sami Toppinen, Porvoo (FI); Jaana Makkonen, Porvoo (FI); Mika Kettunen, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 16/623,306

(22) PCT Filed: Jun. 15, 2018

(86) PCT No.: PCT/EP2018/065973
§ 371 (c)(1),
(2) Date: Dec. 16, 2019

(87) PCT Pub. No.: WO2018/234187
PCT Pub. Date: Dec. 27, 2018

(65) Prior Publication Data
US 2020/0181504 A1    Jun. 11, 2020

(30) Foreign Application Priority Data

Jun. 19, 2017 (FI) .................................... 20175569
Aug. 31, 2017 (FI) .................................... 20175780
(Continued)

(51) Int. Cl.
*C10G 3/00*        (2006.01)
*C07C 45/41*    (2006.01)
(Continued)

(52) U.S. Cl.
CPC .............. *C10G 3/50* (2013.01); *B01D 3/143* (2013.01); *B01J 21/04* (2013.01); *B01J 21/063* (2013.01);
(Continued)

(58) Field of Classification Search
CPC .......... C10G 3/00; C10G 67/02; C07C 45/41; C07C 51/353; C07C 51/367; C11C 1/04; C10L 1/08; B01J 23/78
See application file for complete search history.

(56) References Cited

U.S. PATENT DOCUMENTS 8,679,805 B2    3/2014   Chung et al.
9,523,061 B2   12/2016   Nelson et al.
(Continued)

FOREIGN PATENT DOCUMENTS

CN    1867653 A    11/2006
CN  102300967 A    12/2011
(Continued)

OTHER PUBLICATIONS

Eisner, U. et al. "The synthesis of long-chain, branched, hydroxyaliphatic compounds", Bull. Soc. Chim. FR, pp. 212-218, 1995.
(Continued)

*Primary Examiner* — Youngsul Jeong
(74) *Attorney, Agent, or Firm* — Buchanan Ingersoll & Rooney PC

(57) ABSTRACT

Hydrotreatment of biological oil is disclosed for producing renewable base oil and a diesel oil from low value biological oils. Low value biological oils containing free fatty acids and fatty acid esters can be processed into a renewable base oil and a renewable diesel oil in an efficient manner by first separating at least part of the free fatty acids from the feedstock and then processing separately this free acid feed in a ketonisation reaction followed by hydrodeoxygenation
(Continued)

Scheme for Renewable base oil, diesel and naphtha production and hydroisomerisation reactions to yield a renewable base oil stream. The remaining free fatty acid depleted feed is processed in a separate hydrodeoxygenation and hydroisomerisation step to yield a renewable diesel stream.

24 Claims, 2 Drawing Sheets

(30) Foreign Application Priority Data

| Aug. 31, 2017 | (FI) | ............................. | 20175781 |
|---|---|---|---|
| Aug. 31, 2017 | (FI) | ............................. | 20175782 |
| Dec. 7, 2017 | (FI) | ............................. | 20176095 |

(51) Int. Cl.

| B01J 21/04 | (2006.01) |
|---|---|
| B01J 21/06 | (2006.01) |
| B01J 23/883 | (2006.01) |
| B01J 35/10 | (2006.01) |
| C10G 45/58 | (2006.01) |
| C10L 1/08 | (2006.01) |
| B01J 29/85 | (2006.01) |
| C10G 67/02 | (2006.01) |
| C11C 1/04 | (2006.01) |
| C10M 105/04 | (2006.01) |
| C10M 105/06 | (2006.01) |
| C10M 169/04 | (2006.01) |
| B01D 3/14 | (2006.01) |
| C07C 51/44 | (2006.01) |
| C10M 177/00 | (2006.01) |
| C11C 1/10 | (2006.01) |
| C10N 30/00 | (2006.01) |
| C10N 20/00 | (2006.01) |
| C10N 30/02 | (2006.01) |
| C10N 30/04 | (2006.01) |
| C10N 30/10 | (2006.01) |
| C10N 30/12 | (2006.01) |
| C10N 30/14 | (2006.01) |
| C10N 30/16 | (2006.01) |
| C10N 70/00 | (2006.01) |

(52) U.S. Cl.
CPC ............. *B01J 23/883* (2013.01); *B01J 29/85* (2013.01); *B01J 35/1014* (2013.01); *B01J 35/1019* (2013.01); *B01J 35/1038* (2013.01); *B01J 35/1061* (2013.01); *C07C 45/41* (2013.01); *C07C 51/44* (2013.01); *C10G 3/44* (2013.01); *C10G 3/46* (2013.01); *C10G 3/49* (2013.01); *C10G 45/58* (2013.01); *C10G 67/02* (2013.01); *C10L 1/08* (2013.01); *C10M 105/04* (2013.01); *C10M 105/06* (2013.01); *C10M 169/04* (2013.01); *C10M 177/00* (2013.01); *C11C 1/04* (2013.01); *C11C 1/10* (2013.01); *C10G 2300/1003* (2013.01); *C10G 2300/1014* (2013.01); *C10G 2300/1018* (2013.01); *C10G 2300/202* (2013.01); *C10G 2300/301* (2013.01); *C10G 2300/302* (2013.01); *C10G 2300/304* (2013.01); *C10G 2300/308* (2013.01); *C10G 2300/4006* (2013.01); *C10G 2300/4012* (2013.01); *C10G 2300/4018* (2013.01); *C10G 2400/04* (2013.01); *C10G 2400/10* (2013.01); *C10L 2200/0484* (2013.01); *C10L 2270/026* (2013.01); *C10L 2290/543* (2013.01); *C10M 2203/022* (2013.01); *C10M 2203/0206* (2013.01); *C10M 2203/045* (2013.01); *C10M 2203/065* (2013.01); *C10N 2020/065* (2020.05); *C10N 2020/067* (2020.05); *C10N 2030/02* (2013.01); *C10N 2030/04* (2013.01); *C10N 2030/10* (2013.01); *C10N 2030/12* (2013.01); *C10N 2030/14* (2013.01); *C10N 2030/16* (2013.01); *C10N 2030/43* (2020.05); *C10N 2030/74* (2020.05); *C10N 2070/00* (2013.01)

(56) References Cited

U.S. PATENT DOCUMENTS

| 2005/0077208 A1 | 4/2005 | Miller et al. |
|---|---|---|
| 2005/0263435 A1 | 12/2005 | Skledar et al. |
| 2007/0135663 A1 | 6/2007 | Aalto et al. |
| 2007/0161832 A1 | 7/2007 | Myllyoja et al. |
| 2007/0244018 A1 | 10/2007 | Visger et al. |
| 2008/0034645 A1 | 2/2008 | Bressler |
| 2009/0014354 A1 | 1/2009 | Knuuttila et al. |
| 2010/0234654 A1 | 9/2010 | Wang et al. |
| 2011/0107656 A1 | 5/2011 | Miller |
| 2012/0220506 A1 | 8/2012 | Qin et al. |
| 2013/0190544 A1 | 7/2013 | Wang et al. |
| 2013/0217606 A1 | 8/2013 | Wang et al. |
| 2014/0046104 A1 | 2/2014 | Mcneff et al. |
| 2014/0115955 A1 | 5/2014 | Mcneff et al. |
| 2014/0171703 A1 | 6/2014 | Wang et al. |
| 2014/0323665 A1 | 10/2014 | Wu et al. |
| 2014/0335586 A1 | 11/2014 | Zhang et al. |
| 2015/0018581 A1 | 1/2015 | Kettunen et al. |
| 2015/0018588 A1 | 1/2015 | Myllyoja et al. |
| 2015/0183915 A1 | 7/2015 | Johnson et al. |
| 2015/0251168 A1 | 9/2015 | Kettunen et al. |
| 2016/0137944 A1 | 5/2016 | Liang et al. |
| 2017/0088789 A1 | 3/2017 | Grisso et al. |
| 2017/0240832 A1 | 8/2017 | Hahn et al. |
| 2017/0334806 A1 | 11/2017 | Agee |
| 2017/0362154 A1 | 12/2017 | Kettunen et al. |
| 2018/0171252 A1 | 6/2018 | Fourage et al. |
| 2020/0181503 A1 | 6/2020 | Myllyoja et al. |
| 2020/0181527 A1 | 6/2020 | Kulmala et al. |
| 2021/0139786 A1 | 5/2021 | Toppinen et al. |
| 2021/0139787 A1 | 5/2021 | Myllyoja et al. |

FOREIGN PATENT DOCUMENTS

| CN | 102906229 A | 1/2013 | |
|---|---|---|---|
| CN | 103773442 A | 5/2014 | |
| DE | 102009917827 A1 | 10/2010 | |
| DK | 2809745 A1 | 12/2014 | |
| EP | 1741767 A1 | 1/2007 | |
| EP | 1741768 A1 | 1/2007 | |
| EP | 1741767 B1 * | 7/2015 | ............... C10G 3/00 |
| EP | 2809745 B1 | 4/2016 | |
| EP | 3012310 A1 | 4/2016 | |
| JP | 2004124080 A | 4/2004 | |
| WO | 00/68799 A1 | 11/2000 | |
| WO | 2007061698 A2 | 5/2007 | |
| WO | 2007068795 A1 | 6/2007 | |
| WO | 2007068800 A2 | 6/2007 | |
| WO | 2008152200 A1 | 12/2008 | |
| WO | 2012156679 A1 | 11/2012 | |
| WO | 2013113976 A1 | 8/2013 | |
| WO | 2014099371 A2 | 6/2014 | |
| WO | 2014099373 A1 | 6/2014 | |
| WO | 2016061050 A1 | 4/2016 | |
| WO | 2016062868 A1 | 4/2016 | |

(56) References Cited

FOREIGN PATENT DOCUMENTS

| WO | WO-2016062868 A1 * | 4/2016 | ............ C10G 45/58 |
|----|--------------------|--------|-------------------------|
| WO | 2017001606 A1 | 1/2017 | |

OTHER PUBLICATIONS

Rush, D. et al. "Generation of unusual branched long chain alkanes from hydrous pyrolysis of anamox bacterial biomass", Organic Geochemistry, vol. 76, pp. 136-145, 2014.

Tamai, Y. et al. "Estimation of flow activation volume of synthetic ester lubricants", J. Japan Petrol. Inst., vol. 25, No. 5, pp. 281-285, 1982.

Toubiana, R. et al. "Long-chain aliphatic substances reltaed to bacterial lipids" in Ann. Chim., Paris, FR: 1962, vol. 7, pp. 593-642.

International Search Report (PCT/ISA/210) dated Jul. 19, 2018, by the European Patent Office as the International Searching Authority for International Application No. PCT/EP2018/065971.

International Preliminary Report on Patentability (Chapter of the Patent Cooperation Treaty) (PCT Rule 44bis) (Form PCT/IB/373) dated Dec. 24, 2019 and the Written Opinion of the International Searching Authority (Form PCT/ISA/237) dated Jul. 19, 2018, in the corresponding International Application No. PCT/EP2018/065971 (7 pages).

International Search Report (PCT/ISA/210) dated Jul. 19, 2018, by the European Patent Office as the International Searching Authority for International Application No. PCT/EP2018/065973.

International Preliminary Report on Patentability (Chapter of the Patent Cooperation Treaty) (PCT Rule 44bis) (Form PCT/IB/373) dated Dec. 24, 2019 and the Written Opinion of the International Searching Authority (Form PCT/ISA/237) dated Jul. 19, 2018, in the corresponding International Application No. PCT/EP2018/065973. (6 pages).

Deffense Etienne, "From Organic Chemistry to Fat and Oil Chemistry", OCL, vol. 16, No. 1, 2009, pp. 14-24.

International Search Report (PCT/ISA/210) and Written Opinion (PCT/ISA/237) received for PCT Application No. PCT/EP2018/065976, dated Aug. 27, 2018, 11 pages.

International Search Report (PCT/ISA/210) and Written Opinion (PCT/ISA/237) received for PCT Application No. PCT/EP2018/065978, dated Sep. 13, 2018, 16 pages.

International Search Report (PCT/ISA/210) and Written Opinion (PCT/ISA/237) received for PCT Application No. PCT/EP2018/065980, dated Jul. 25, 2018, 10 pages.

Non Final Office Action dated Mar. 31, 2021, by the U.S. Patent and Trademark Office in U.S. Appl. No. 16/623,188, 10 pages.

Non Final Office Action dated Nov. 5, 2020, by the U.S. Patent and Trademark Office in U.S. Appl. No. 16/623,257, 8 pages.

Restriction Requirement dated Jan. 28, 2021, by the U.S. Patent and Trademark Office in U.S. Appl. No. 16/623,276, 7 pages.

Notice of Allowance dated Jun. 18, 2021, by the U.S. Patent and Trademark Office in U.S. Appl. No. 16/623,210.

Notice of Allowance dated Jul. 12, 2021, by the U.S. Patent and Trademark Office in U.S. Appl. No. 16/623,188.

Notice of Allowance dated Jul. 15, 2021, by the U.S. Patent and Trademark Office in U.S. Appl. No. 16/623,257.

Office Action dated Jul. 2, 2021, by the U.S. Patent and Trademark Office in U.S. Appl. No. 16/623,276.

First Office Action dated Jul. 2, 2021, by the Chinese Patent Office in corresponding Chinese Patent Application No. 201880039835.4, and an English Translation of the Office Action. (7 pages).

* cited by examiner

Figure 1 – Scheme for Renewable base oil production
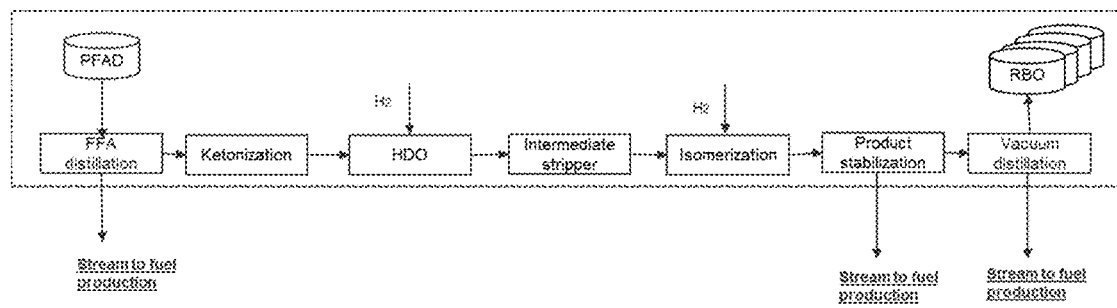
Figure 2 – Scheme for Renewable base oil, diesel and naphtha production
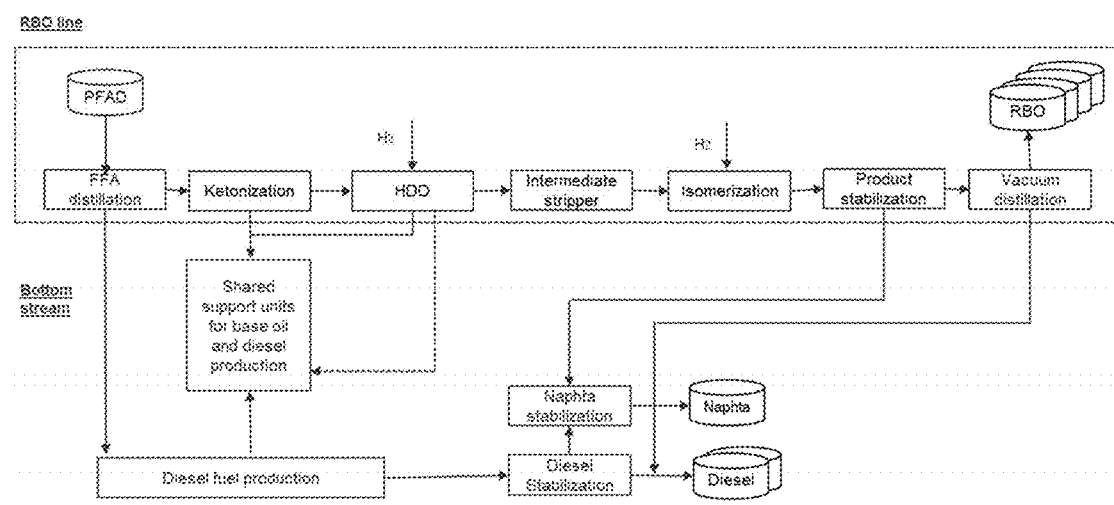

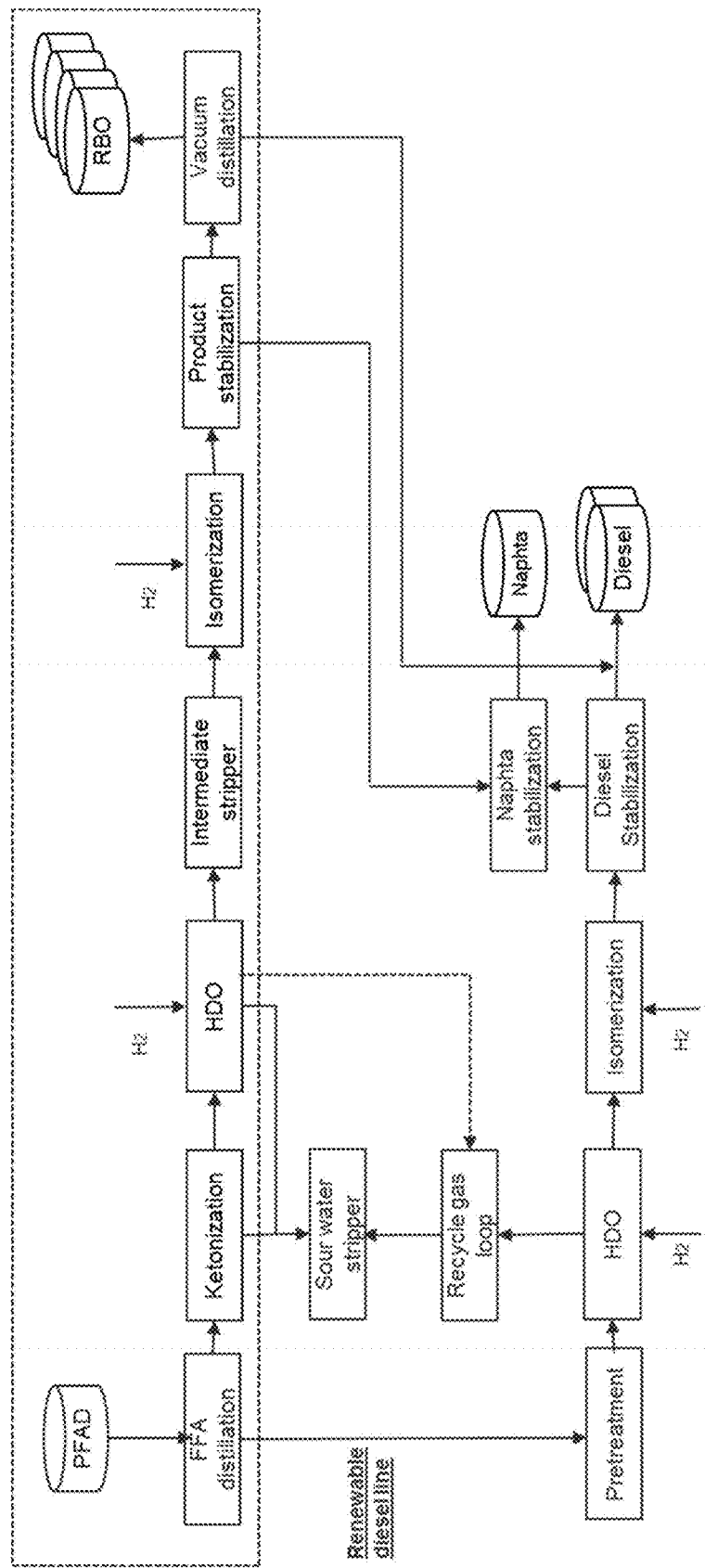
Figure 3 – Scheme for Renewable base oil, diesel and naphtha production

PROCESS FOR THE PRODUCTION OF RENEWABLE BASE OIL, DIESEL AND NAPHTHA

TECHNICAL FIELD

The present invention relates to the field of hydrotreatment of biological oil, in particular to methods for producing renewable base oil and a diesel oil, such as methods for producing renewable base oil, a diesel oil and naphtha in a process efficient manner, and in particular with reduced hydrogen consumption and increased catalyst life time.

BACKGROUND ART

The technology relating to hydrotreatment of biological oils, such as plant oils and animal fats has received much attention since the combined steps of hydrodeoxygenation and hydroisomerisation of plant oils was first found to result in a renewable diesel with improved cold flow properties back in the last years of the 20$^{th}$ century. In the beginning of the 21$^{st}$ century the manufacture of renewable base oil has also been investigated through a number of routes, including double-bond oligomerisation of renewable oils or ketonisation reactions of fatty acids.

The hydrotreatment of biological oils are for the most part catalysed. Catalytic hydrotreatment of biological oils on an industrial scale (>100 kt biological oil annually) faces several challenges, such as the time that the plant or reactor can remain on-stream before maintenance is required. One of the causes for reduced times on-stream is the deactivation of the catalyst, or the physical plugging of the catalyst bed, causing an increased and undesired pressure drop. The catalyst life time is highly dependent on the quality of the feedstock. One of the challenges of catalytic hydrotreatment is the catalyst life time, in particular in combination with the processing of more degraded feeds comprising glycerides together with certain amounts of more reactive free fatty acids (FFA), compared to less degraded biological oils, such as for example edible rapeseed oil, which has very low amounts of free fatty acids. Another challenge in the hydrotreatment of biological oils is to reduce the overall hydrogen amount needed to convert the biological oil to renewable diesel or to renewable base oil.

EP 1 741 768 (to Neste Oyj) provides a solution to the undesired side reactions in the manufacture of diesel starting from a biological oil having more than 5 wt % free fatty acids. It was found that diluting the free fatty acid containing feed with a large amount of hydrocarbon diluting agent reduced the undesired side reactions, allowing for improved catalyst life time and thus more time on-stream.

There is a desire to use renewable oils that cannot be used for human consumption. The biological oils used for processing into renewable diesel and renewable base oils continues to become more and more degraded as well as more complex compared to examples of pure triglyceride feeds sometimes given in the prior art. Accordingly, there is a need in the art for processes that can utilise such degraded and complex biological oils or mixtures thereof that contain varying amounts of free fatty acids, in particular for the preparation of renewable diesel and renewable base oil.

WO 2007/068795 A1 (to Neste Oil Oyj) describes (see e.g. FIG. 1 of that application) a complex feed which is diluted with hydrocarbons and processed by prehydrogenation, ketonisation, hydrodeoxygenation, stripping, hydroisomerisation, optional hydrofinishing, and distillation into a renewable base oil, renewable diesel as well as a renewable gasoline.

There is still a need for further processes that can process low-value biological oils containing free fatty acids and fatty acid esters into renewable base oils and renewable diesel in an manner that is efficient with regards to e.g. catalyst life time and hydrogen consumption.

SUMMARY OF THE INVENTION

The present invention was made in view of the prior art described above, and the object of the present invention is to provide a more efficient processing method of renewable oils having a certain amount of free fatty acids, in particular, but not limited to lower hydrogen consumption and/or increased catalyst life time.

To solve the problem, the present invention provides a method for producing a renewable base oil and a diesel fuel from a feedstock of biological origin, the method comprising: a) providing a feedstock, the feedstock comprising 2-95 wt % of a mixture of free fatty acids; 5-98 wt % fatty acid glycerols selected from mono-glycerides, di-glycerides and tri-glycerides of fatty acids; 0-50 wt % of one or more compounds selected from the list consisting of: fatty acid esters of the non-glycerol type, fatty amides, and fatty alcohols; the major part of the feedstock being the mixture of free fatty acids and fatty acid glycerols; b) separating the feedstock into at least: a free fatty acid feed having a higher concentration of free fatty acids than the feedstock, the free fatty acids comprising $C_{10}$-$C_{24}$ fatty acids, preferably $C_{14}$-$C_{22}$, such as $C_{14}$, $C_{16}$, $C_{18}$, $C_{20}$ and $C_{22}$ fatty acids; and one or more free fatty acid depleted feed(s) having higher concentration of the compounds selected from mono-glycerides, di-glycerides and tri-glycerides of fatty acids, and having a higher boiling point than the free fatty acid feed; c) subjecting the fatty acid feed to ketonisation reaction conditions where two fatty acids react to yield a ketone stream, the ketone stream comprising as the major part (saturated) ketones; d) subjecting the ketone stream to both hydrodeoxygenation reaction conditions and to hydroisomerisation reaction conditions, simultaneously or in sequence, to yield a deoxygenated and isomerised base oil stream comprising the renewable base oil; e) optionally distilling the product of step d) to obtain a distilled renewable base oil; f) where the one or more free fatty acid depleted feed(s) is transformed into a diesel product, preferably by subjecting the one or more free fatty acid depleted feed(s) to both hydrodeoxygenation reaction conditions and to hydroisomerisation reaction conditions, simultaneously or in sequence, to yield a deoxygenated and isomerised diesel stream comprising the diesel fuel; optionally distilling the stream obtained from step f) to obtain a distilled diesel fuel.

That is, the inventors of the present invention in a first aspect of the invention found that degraded low-value biological oils containing free fatty acids and fatty acid esters can be processed into a renewable base oil and a renewable diesel oil in an efficient manner by first separating at least part of the free fatty acids from the feedstock and then processing this free acid feed separately in a ketonisation reaction followed by hydrodeoxygenation and hydroisomerisation reactions to yield a renewable base oil stream. The remaining free fatty acid depleted feed is processed in a separate hydrodeoxygenation and hydroisomerisation step to yield a renewable diesel fuel stream.

Separating the feedstock into two separate streams provides surprising advantages compared to a combined treatment of the entire feedstock, in that the ketonisation reaction of the separated feed having mainly free fatty acids may be run under conditions that result in almost complete (>90%, >95%, >99% or even ≥99.5%) conversion of the free fatty acids into ketones, as there is less undesired oligomerisation reaction compared to ketonisation of the entire stream. Furthermore, this ketone stream may be converted under milder hydrodeoxygenation conditions into the corresponding paraffin, compared to a feed that also comprise unconverted fatty acids or triglycerides.

As an additional advantage, the fatty acid depleted feed will contain less of the free fatty acids compared to the (initial) feedstock and therefore use less hydrogen compared to the hydrogenation of the entire feedstock. This results in less overall hydrogen consumption due to the ketonisation reaction of the separate free fatty acid feed, because during ketonisation, 75% of the oxygen content of the fatty acids is removed as $CO_2$ and $H_2O$ without consuming hydrogen, and consequently that less hydrogen is required to convert the ketone stream. Accordingly, the separation of the feed results in less overall hydrogen consumption, milder hydrodeoxygenation conditions for the ketone stream, when complete ketonisation conversion can be achieved, i.e. no unconverted fatty acids which needs more reaction conditions. Fatty acids are also very corrosive and might produce side reactions during HDO. Therefore a longer time on-stream for the reactor comprising the hydrodeoxygenation catalyst can be achieved, because it is exposed to less of the free fatty acids compared to a hydrotreatment of the same feed that has not undergone any prior separation.

The process may additionally be for producing a naphtha fuel, where the naphtha fuel is obtained from distillation of both the deoxygenated and isomerised base oil stream of step d) and from the distillation of the deoxygenated and isomerised diesel stream of step f).

Prior to step a) of the method, an initial feedstock comprising fatty acid esters may be pre-treated in at least a hydrolysis step thereby producing the feedstock, where the ratio of free fatty acids to fatty acid esters has been increased compared to the initial feedstock.

In certain variants, no pre-treatment by hydrogenation or by hydrolysis may be done in or in-between steps a)-c).

When the hydrodeoxygenation and hydroisomerisation of step d) takes place in sequence, there may be in-between the hydrodeoxygenation and hydroisomerisation steps a stripping step, where gasses are separated from liquids. This may occur in a high temperature and high pressure separation step, for example at a temperature between 300-330° C. and pressure between 40-50 barg.

Between steps d) and e) of the method, there may be a stripping step, where gasses are separated from liquids. This may be done at a temperature between 320-350° C. and pressure between 3-6 barg.

The major part of the free fatty acid feed may be saturated free fatty acids. The major part of the free fatty acid feed may be $C_{16}$ fatty acids. The feedstock may be palm oil fatty acid distillate (PFAD).

The ketonisation reaction conditions may comprise one or more of the following: a temperature in the range from 300 to 400° C.; a pressure in the range from 5 to 30 barg; a WHSV in the range from 0.25-3 $h^{-1}$. The ketonisation reaction may be in the presence of a ketonisation catalyst, the ketonisation catalyst comprising a metal oxide catalyst. The ketonisation reaction may be in the presence of a gas in the range from 0.1-1.5 gas/feed ratio (w/w), the gas being selected from one or more of: $CO_2$, $H_2$, $N_2$, $CH_4$, $H_2O$.

The ketonisation reaction conditions may be selected such as to ensure liquid phase ketonisation.

The ketonisation catalyst may be a metal oxide catalyst selected from the list consisting of one or more of: Ti, Mn, Mg, Ca, and Zr containing metal oxide catalyst.

The ketonisation catalyst may be $TiO_2$, optionally on a support. For example $TiO_2$ in anatase form having an average pore diameter of 80-160 Å, and/or a BET area of 40-140 $m^2/g$, and/or porosity of 0.1-0.3 $cm^3/g$.

The hydrodeoxygenation reaction conditions may comprise one or more of the following: a temperature in the range from 250 to 400° C.; a pressure in the range from 20 to 80 barg; a WHSV in the range from 0.5-3 $h^{-1}$; and a $H_2$ flow of 350-900 nl $H_2$/l feed. The hydrodeoxygenation reaction may be performed in the presence of a hydrodeoxygenation catalyst, such as NiMo on an alumina support.

The isomerisation reaction conditions may comprise one or more of the following: a temperature in the range from 250 to 400° C.; a pressure in the range from 10 to 60 barg; a WHSV in the range from 0.5-3 $h^{-1}$; a $H_2$ flow of 100-800 nl $H_2$/l feed. The hydroisomerisation reaction may be in the presence of an isomerisation catalyst, such as a catalyst comprising a Group VIII metal and a molecular sieve, optionally on an alumina and/or silica support.

The hydrodeoxygenation and isomerisation catalyst may be the same, such as for example NiW.

BRIEF DESCRIPTION OF THE DRAWINGS

FIG. 1 shows a schematic overview of renewable base oil production.

FIG. 2 shows a schematic overview of renewable base oil production, with additional shared support units for base oil and diesel production, for example in the form of sour water stripper and recycle gas loop, as well as optional naphtha and/or diesel production.

FIG. 3 shows a schematic overview of an integrated renewable base oil, diesel and naphtha production, with additional and optional sour water stripper and recycle gas loop.

DETAILED DESCRIPTION OF THE INVENTION

In describing the embodiments of the invention specific terminology will be used for the sake of clarity. However, the invention is not intended to be limited to the specific terms so selected, and it is understood that each specific term includes all technical equivalents which operate in a similar manner to accomplish a similar purpose.

The object of the present invention is to provide a more efficient processing method of renewable oils having a certain amount of free fatty acids, in particular, but not limited to lower hydrogen consumption and increased catalyst life time.

Provided by the present invention a method for producing a renewable base oil and a diesel fuel from a feedstock of biological origin, the method comprising: a) providing a feedstock, the feedstock comprising 2-95 wt % of a mixture of free fatty acids; 10-98 wt % fatty acid glycerols selected from mono-glycerides, di-glycerides and tri-glycerides of fatty acids; 0-50 wt % of one or more compounds selected from the list consisting of: fatty acid esters of the non-glycerol type, fatty amides, and fatty alcohols; the major part of the feedstock being the mixture of free fatty acids and fatty acid glycerols; b) separating the feedstock into at least: a free fatty acid feed having a higher concentration of free fatty acids than the feedstock, the free fatty acids comprising $C_{10}$-$C_{24}$ fatty acids, preferably $C_{14}$-$C_{22}$, such as $C_{14}$, $C_{16}$, $C_{18}$, $C_{20}$ and $C_{22}$ fatty acids; and one or more free fatty acid depleted feed(s) having higher concentration of the compounds selected from mono-glycerides, di-glycerides and tri-glycerides of fatty acids, and having a higher boiling point than the free fatty acid feed; c) subjecting the fatty acid feed to ketonisation reaction conditions where two fatty acids react to yield a ketone stream, the ketone stream comprising as the major part ketones; d) subjecting the ketone stream to both hydrodeoxygenation reaction conditions and to hydroisomerisation reaction conditions, simultaneously or in sequence, to yield a deoxygenated and isomerised base oil stream comprising the renewable base oil; e) optionally distilling the product of step d) to obtain a distilled renewable base oil; f) where the one or more free fatty acid depleted feed(s) is transformed into a diesel product, preferably by subjecting the one or more free fatty acid depleted feed(s) to both hydrodeoxygenation reaction conditions and to hydroisomerisation reaction conditions, simultaneously or in sequence, to yield a deoxygenated and isomerised diesel stream comprising the diesel fuel; optionally distilling the stream obtained from step f) to obtain a distilled diesel fuel.

That is, the inventors of the present invention in a first aspect of the invention found that degraded low-value biological oils containing free fatty acids and fatty acid esters can be processed into a renewable base oil and a renewable diesel oil in an efficient manner by first separating at least part of the free fatty acids from the feedstock and then processing this free acid feed separately in a ketonisation reaction followed by hydrodeoxygenation and hydroisomerisation reactions to yield a renewable base oil stream.

The remaining free fatty acid depleted feed is processed in a separate hydrodeoxygenation and hydroisomerisation step to yield a renewable diesel stream. Separating the feedstock into two separate streams provides surprising advantages compared to a combined treatment of the entire feedstock, in that the ketonisation reaction of the separated feed having mainly free fatty acids may be run under conditions that result in almost complete (>90%, >95%, >99% or even ≥99.5%) conversion of the free fatty acids into ketones, as there is less undesired oligomerisation reaction compared to ketonisation of the entire stream. Furthermore, this ketone stream may be converted under milder hydrodeoxygenation conditions into the corresponding paraffin, compared to a feed that also comprise triglycerides.

As an additional advantage, the fatty acid depleted feed will contain less of the free fatty acids compared to the (initial) feedstock and therefore use less hydrogen compared to the hydrogenation of the entire feedstock. This results in less overall hydrogen consumption due to the ketonisation reaction of the separate free fatty acid feed, because during ketonisation, 75% of the oxygen content of the fatty acids is removed as $CO_2$ and $H_2O$ without consuming hydrogen, and consequently that less hydrogen is required to convert the ketone stream. Accordingly, the separation of the feed results in less overall hydrogen consumption, milder hydrodeoxygenation conditions for the ketone stream, i.e. more energy efficient, as well as a longer time on-stream for the reactor comprising the hydrodeoxygenation catalyst, because it is exposed to less of the free fatty acids compared to a hydrotreatment of the same feed that has not undergone any prior separation.

The method for producing a renewable base oil and a diesel fuel from a feedstock of biological origin, of the present invention will now be explained in more details.

The renewable base oil according to the present invention may be highly paraffinic in that it is derived from ketonisation of fatty acids. Accordingly, the renewable base oil may comprise very little aromatics or oxygenates. Being a base oil, it boils within a base oil boiling range, such as above 380° C.

Renewable base oil in the context of the present invention is to be understood as a base oil being obtained from one or more renewable sources. Base oil is a well-known term, and base oil in the context of the present invention is can be defined as a hydrocarbon based composition with a viscosity index above 80, for example the base oil in the context of the present invention can be even further defined as fulfilling the requirements of the API base oil groups I, II or III, preferably API group III.

The base oil affects many parameters of their end products or application such as the viscosity, oxidation stability, volatility, cold flow properties such as pour point, and viscosity index.

Base oils which can be manufactured from ketones obtained according to the present invention may fulfil the requirement of Group III of The American Petroleum Institute (API) which divides base oils into five main groups. Groups I to III are petroleum base oil of varying qualities.

TABLE 1

| API base stock categories | | | |
|---|---|---|---|
| Group | Sulfur, wt-% | | Saturates, % | Viscosity Index (VI) |
| I | >0.03 | and/or | <90 | 80-119 |
| II | ≤0.03 | and | ≥90 | 80-119 |
| III | ≤0.03 | and | ≥90 | ≥120 |
| IV | Synthetic poly-alpha-olefins (PAOs) | | | |
| V | Any other type of base oil than group I-IV | | | |

A renewable diesel fuel (or renewable diesel fuel component) is a hydrocarbon diesel product as opposed to e.g. oxygen-containing biodiesel, which are mono-alkyl fatty acid esters of biological oils. Being a diesel fuel, it boils within a diesel boiling range, such as between 180 and 380° C., for example between 180° C. and 350° C. As an example diesel fuel according to EN15940 or for example a diesel fuel component for a diesel fuel according to EN 590.

Common to the renewable base oil, diesel or naphtha are that they may be highly paraffinic, in that the content of aromatics and/or oxygenates is very low, such as below 0.5 vol %.

The renewable content may be determined from the starting materials, as well as being determined in the products by isotopic distribution involving $^{14}C$, $^{13}C$ and/or $^{12}C$ as described in ASTM D6866. Reference is made to WO 200/068799, which is hereby incorporated by reference. For example, typical $^{14}C$ isotope content of the total carbon content in the product, which is completely of biological origin, is at least 100%. Accordingly, a renewable base oil made from a feedstock of biological origin will be at least 100%.

Feedstock

A feedstock is provided. The feedstock comprises as the major part a mixture of free fatty acids and fatty acid esters, such as fatty acid glycerols. This is because the ketonisation reaction requires free fatty acids and because degraded or low-value biological oils are typically mixtures of free fatty acids and fatty acid glycerols, such as triglycerides or partial glycerides. The major part of the free fatty acids and fatty acid esters may be considered to be more than 50 wt %, such as more than 70 wt %, more than 90 wt %.

In degraded biological oil, part of the triglycerides, which can be used as high-value edible oils have been degraded to free fatty acids and partial glycerides, such as mono- and di-glycerides. The low-value biological oils may therefore have a higher amount of free fatty acids compared to the glyceride content (combined amount of mono-, di- and tri-glycerides). For example, in the refining of crude palm oil, a palm oil stripper may be used to separate crude palm oil into high-value edible palm oil and low-value palm oil fatty acid distillate (PFAD). The low-value PFAD is not fit for human consumption, and may advantageously be used in the methods according to the present invention.

Accordingly, the feedstock may be palm oil fatty acid distillate (PFAD), which contains as the major part free fatty acids. PFAD is one example of low-value biological oils containing free fatty acids and fatty acid esters, such as partial glycerides. Such degraded fats are unsuited for food production and need to be removed during the palm oil refining process before the palm oil meets the food industry's quality standards. The fatty acid composition of PFAD varies by source. It is typically desirable to keep the degraded free fatty acid content low in edible oils, such as palm oil, which is for the most part comprises of triglycerides. PFAD is a by-product that is unsuited for food production. It has a higher content of free fatty acids than triglycerides (because the palm oil triglycerides are used as the edible palm oil), such as a higher amount of free fatty acids compared to the fatty acid ester content.

Palm oil fatty acid distillate (PFAD) is a by-product from refining crude palm oil. It is a light brown semi-solid at room temperature, which melts to a brown liquid on heating. While the composition of PFAD varies, the minimum free fatty acid (FFA) content of PFAD may be 60 wt %. The contractual specifications the providers of PFAD are asked to fulfil often specifies 70 wt % or more FFA, which means that the FFA content is often 80 wt % or more. The FFA content may be in the range of 65-95 wt %, such as between 80-90 wt %.

The PFAD also contains fatty acid glycerols selected from mono-glycerides, di-glycerides, and tri-glycerides of fatty acids. For example the fatty acid glycerol content may be above 2 wt % or below 20 wt %, for example in the range of 2-15 wt %.

The remaining components of PFAD may be unsaponifiable matters, such as tocopherol, tocotrienols, sterols, squalenes, and volatile substances. For example, the unsaponifiable matter content may be above 0.5 wt % or below 3 wt %, for example in the range of 0.5-2.5 wt %.

PFAD may additionally comprise trace metals, for example Cr, Ni, Cu, Fe.

Bonnie Tay Yen Ping and Mohtar Yusof published in 2009 Characteristics and Properties of Fatty Acid Distillates from Palm Oil in Oil Palm Bulletin 59, p. 5-11, which provide updated information on the composition of PFAD, which is incorporated herein by reference.

While one example of a feedstock of biological origin according to the present invention is PFAD, there are many other well-suited feedstocks of biological origin, such as other plant oils or animal fat that have contain free fatty acids, various grades of and products from the refining of plant oil or animal fat, waste cooking oil, various grades of and products from tall oil refining, crude tall oil (CTO), tall oil, tall oil heads, tall oil fatty acids (TOFA), yellow grease, poultry fat, fish oil or acid oil side products of for example oleochemicals production.

The feedstock of biological origin may further be mixtures of a number of different feedstocks of biological origin. For example one or more kinds of plant oils or animal fats having more free fatty acids than fatty acid esters mixed with one or more kinds of plant oils or animal fats having less free fatty acids than fatty acid esters.

While the feedstock comprises as the major part a mixture of free fatty acids and fatty acid esters, such as fatty acid glycerols, the amounts of FFA and of fatty acid esters may vary considerably as evident from the many different types of the free fatty acid content and fatty acid ester feedstocks and mixtures mentioned above.

For practical purposes the feedstock may comprise at least 2 wt % free fatty acids, such as at least 5 wt %. For example, some separation methods, such as distillation, are more efficient when the mixture of free fatty acids is at least 5 wt %, such as at least 7 wt % or 10 wt %. The free fatty acid content may be below 98 wt %, such as below 95 wt %, or below 90 wt %.

For practical purposes the feedstock may comprise at least 2 wt % fatty acid esters, such as at least 5 wt %. For example, some separation methods, such as distillation, are more efficient when the content of fatty acid esters is at least 5 wt %, such as at least 7 wt % or at least 10 wt %. The fatty acid ester content may be below 98 wt %, such as below 95 wt %, or below 90 wt %.

For example the mixture of free fatty acids may be 2-95 wt %, for example 5-95 wt %, such as 5-90 wt % of a mixture of free fatty acids. In some feedstocks, the free fatty acid content is rather high, such as above 50 wt % or above 70 wt %.

For example the mixture of fatty acid glycerols selected from mono-glycerides, di-glycerides and tri-glycerides of fatty acids may be 5-98 wt %, for example 5-95 wt %, such as 5-90 wt % of a mixture of free fatty acids. In some feedstocks, the free fatty acid content is rather high, such as above 50 wt % or above 70 wt %.

The feedstock may for example comprise 5-90 wt % free fatty acids, 5-90 wt % fatty acid glycerols, and 0-20 wt % of one or more compounds selected from the list consisting of: fatty acid esters of the non-glycerol type, fatty amides, and fatty alcohols, where the feedstock comprises more than 50 wt % of free fatty acids and fatty acid glycerols, such as 70 wt % or more, for example 80 wt % or more.

It is possible to increase the fatty acid content of the feedstock thereby potentially providing more renewable base oil in the process by prior to step a) of the method, an initial feedstock comprising fatty acid esters may be pretreated in at least a hydrolysis step, such as partial hydrolysis, thereby producing the feedstock, where the ratio of free fatty acids to fatty acid esters has been increased compared to the initial feedstock.

The term fatty acid is well-known to the skilled person, and have been used to characterise a carboxylic acid consisting of a hydrocarbon chain and a terminal carboxyl group, in particular any of those carboxylic acids occurring as esters in fats and oils.

The fatty acids may be saturated and unsaturated. When desiring to manufacture dimer products in the ketonisation reaction, it is advantageous that the fatty acids are saturated fatty acids or have a reduced amount of unsaturation because double bond oligomerisations, which may lead to tarry products, are then avoided or reduced. For example the major part of the free fatty acid feed may be saturated free fatty acids. Advantageously, more than 90 wt % of the free fatty acid feed is saturated fatty acids, such as more than 95 wt % or more than 99 wt %.

The saturated fatty acids may be obtained from a double-bond hydrogenation reaction of either the feedstock prior to separating it into a free fatty acid feed and one or more free fatty acid depleted feed(s) or double bond hydrogenation of the free fatty acid feed after separation. For example a prehydrogenation step may utilise a hydrogenating catalyst, for example as described below under the heading "Hydrodeoxygenation of the ketone stream"—for example NiMo on an alumina support, but preferably double bond hydrogenation is done with supported a noble metal, such as Pd or Pt on Silica or carbon support, which tends to be efficient in double bond hydrogenation. The prehydrogenation may be conducted at a temperature below 300° C., such as below 280° C. or below 260° C. in order to avoid hydrodeoxygenation reactions. The prehydrogenation may also be above 90° C., such as above 110° C. or above 120° C. in order to be high enough to ensure sufficient hydrogenation of the double bonds. For example the temperature for prehydrogenation may be 90-300° C., such as 110-280° C., for example 120-260° C. The pressure may be 10-70 barg, such as 20-60 barg, for example 30-50 barg. The WHSV may be 0.5-3.0 $h^{-1}$, such as 1.0-2.5 $h^{-1}$, for example 1.0-2.0 $h^{-1}$. The $H_2$/oil ratio may be 100-500 nl/l, such as 150-450 nl/l, for example 200-400 nl/l. Accordingly, the prehydrogenation may preferably be conducted at 90-300° C., 10-70 barg, WHSV of 0.5-3.0 $h^{-1}$, and $H_2$/oil ratio of 100-500 nl/l; more preferably at 110–280° C., 20-60 barg, WHSV of 1.0-2.5 $h^{-1}$, and $H_2$/oil ratio of 150-450 nl/l; even more preferably at 120–260° C., 30-50 barg, WHSV of 1.0-2.0 $h^{-1}$, and $H_2$/oil ratio of 200-400 nl/l.

The saturated fatty acids may also be present in the feedstock itself, and separation may further improve the part of free fatty acids that are saturated. For example PFAD typically contains around 30-40 wt % $C_{16}$ saturated fatty acids together with around 50 wt % $C_{18}$ saturated and unsaturated fatty acids, and less than 5 wt % fatty acids below $C_{14}$. This makes PFAD or PFAD containing mixtures advantageous feedstocks because the large amount of $C_{16}$ saturated fatty acids can be separated from the remaining feedstock, thereby obtaining a free fatty acid feed having a higher amount of free fatty acids, in particular having a higher amount of saturated free fatty acids, which are advantageous when wanting to manufacture dimer products in the ketonisation reaction.

Separation of the Feedstock

The method involves a step b) of separating the feedstock into at least: a free fatty acid feed having a higher concentration of free fatty acids than the feedstock.

The separation step may for example be distillation, but other methods, such as crystallisation by cooling or a combination of distillation and crystallisation, may be used.

The separation may for example be distillation, such as at a temperature between 100° C. to 300° C. and at a distillation pressure of 0.5 kPa to 5 kPa.

The free fatty acids of the free fatty acid feed may be $C_{10}$-$C_{24}$ fatty acids, preferably $C_{14}$-$C_{22}$, such as one or more of $C_{14}$, $C_{16}$, $C_{18}$, $C_{20}$ and $C_{22}$ fatty acids The one or more free fatty acid depleted feed(s) has a higher concentration of the compounds selected from mono-glycerides, di-glycerides and tri-glycerides of fatty acids compared to the feedstock of biological origin. For example, the one or more free fatty acid depleted feed(s) may have a concentration that is at least 5% higher, such as at least 25% higher, of the compounds selected from mono-glycerides, di-glycerides and tri-glycerides of fatty acids compared to the feedstock of biological origin. For example, the one or more free fatty acid depleted feed(s) may have a content of free fatty acids that is below 2 wt %.

For example, the free fatty acid feed may have a concentration that is at least 5% higher, such as at least 25% higher, of the compounds selected from mono-glycerides, di-glycerides and tri-glycerides of fatty acids compared to the feedstock of biological origin. For example, the free fatty acid feed may have a content of fatty acid glycerols selected from mono-glycerides, di-glycerides and tri-glycerides of fatty acids that is below 5 wt %.

The one or more free fatty acid depleted feed(s) may have a higher boiling point than the free fatty acid feed and/or have a higher average molecular weight. For example the higher boiling point can be a higher final boiling point compared to the free fatty acid feed and the higher average molecular weight can be measured as a weighted average. The boiling points may for example be measured using SimDist GC boiling point plots according to ASTM D 2887.

The feedstock usually contains both $C_{16}$ and $C_{18}$ fatty acids, which may be separated by distillation for example, and the major part of the free fatty acid feed may be $C_{16}$ fatty acids.

Ketonisation

The fatty acid feed that has been separated from the feedstock is in step c) subjected to ketonisation reaction conditions where two fatty acids react to yield a ketone stream, the ketone stream comprising as the major part ketones.

The ketonisation reaction yields both water and carbon dioxide, which may be separated from the oil fraction, for example water may be separated by decanting, and carbon dioxide and other gaseous components may be separated in a flash drum.

The ketonisation reaction conditions may comprise one or more of the following: a temperature in the range from 300 to 400° C.; a pressure in the range from 5 to 30 barg; a WHSV in the range from 0.25-3 $h^{-1}$.

For example the ketonisation reaction conditions may involve a temperature in the range from 300 to 400° C.; a pressure in the range from 5 to 30 barg; a WHSV in the range from 0.25-3 $h^{-1}$. Preferably the ketonisation reaction conditions may involve a temperature in the range from 330 to 370° C.; a pressure in the range from 10 to 25 barg; a WHSV in the range from 0.5-2 $h^{-1}$. More preferably the ketonisation reaction conditions may involve a temperature in the range from 340 to 360° C.; a pressure in the range from 15 to 20 barg; a WHSV in the range from 1.0-1.5 $h^{-1}$.

The ketonisation reaction is usually conducted in the presence of a ketonisation catalyst, the ketonisation catalyst comprising a metal oxide catalyst. For example, the ketonisation catalyst may be a metal oxide catalyst selected from the list consisting of one or more of: Ti, Mn, Mg, Ca, and Zr containing metal oxide catalyst. For example, the ketonisation catalyst may be $TiO_2$, such as for example $TiO_2$ in anatase form having an average pore diameter of 80-160 Å, and a BET area of 40-140 $m^2$/g, and porosity of 0.1-0.3 $cm^3$/g.

The ketonisation reaction may be pressurised by a gas. For example the ketonisation may be conducted in the presence of a gas in the range from 0.1-1.5 gas/feed ratio (w/w), the gas being selected from one or more of: $CO_2$, $H_2$, $N_2$, $CH_4$, $H_2O$. The gas used for pressurisation may advantageously be $CO_2$ as it is produced as a by-product of the ketonisation reaction and can be recycled as a pressurisation gas.

The ketonisation reaction conditions may be selected such as to ensure liquid phase ketonisation or at least that the feed introduction to the ketonisation step is in liquid form. By ensuring liquid phase ketonisation, by suitable selection of a combination of catalyst, pressure and temperature, the reaction results in less undesired by-products, compared to gas phase ketonisation. Gas phase ketonisation normally needs high gas recycle in order to transfer fatty acids from solid/liquid form to gas phase, due to the high boiling points of fatty acids. This means that the reactor system for the gas phase ketonisation must be bigger and more complex; this will increase the investment costs significantly.

The ketone stream comprises dimers of the free fatty acid feed. For example, if the free fatty acid feed is exclusively palmitic acid (C16:0 fatty acid), then the ketone stream will produce a $C_{31}$ ketone, and if the free fatty acid feed is a mixture of $C_{16}$ and $C_{18}$ fatty acids, then the ketone stream will produce a mixture of $C_{31}$, $C_{33}$, and $C_{35}$ ketones.

As mentioned above, the free fatty acid stream may be a saturated free fatty acid feed. This reduces the amount of unwanted oligomerisation product. If the free fatty acid feed contains unsaturated free fatty acids, these free fatty acids may be saturated by hydrogenation. Such a prehydrogenation step is usually conducted under mild conditions in the presence of a hydrogenation catalyst at temperatures between 50 and 400° C., under a hydrogen pressure ranging from 0.1 to 20 MPa, preferably at temperatures between 150 and 300° C., under a hydrogen pressure ranging from 1 to 10 MPa. The prehydrogenation catalyst contains metals of the Group VIII and/or VIA of the periodic system of the elements. The prehydrogenation catalyst is preferably a supported Pd, Pt, Rh, Ru, Ni, Cu, CuCr, NiMo or CoMo catalyst, the support being activated carbon, alumina and/or silica.

However, it is desirable that no hydrogenation of free fatty acids is done. In particular the palmitic acid (saturated free fatty acid) in PFAD may be separated by distillation, thus yielding a saturated free fatty acid feed of palmitic acid without any hydrogenation necessary.

Accordingly, in certain variants of the present invention, no pre-treatment by hydrogenation or by hydrolysis is done in or in-between steps a)-c).

The ketonisation reaction of the free fatty acid feed may be run under conditions that result in almost complete (>90%, >95%, >99% or even ≥99.5%) conversion of the free fatty acids into ketones, as there is less undesired oligomerisation reaction compared to ketonisation of the entire stream. This provides distinct advantages downstream in that hydrodeoxygenation of the ketone stream requires less severe hydrodeoxygenation conditions in order to ensure complete deoxygenation of the ketone feed, compared to e.g. the free fatty acid depleted feed, which may contain both free fatty acids and fatty acid glycerols. Less severe conditions, for example lower reaction temperature in the hydrodeoxygenation step results in less energy used, a reduction in undesirable side reactions, such as coking, leading to a longer catalyst life time.

Hydrodeoxygenation of the Ketone Stream

The ketone stream obtained from the ketonisation reaction may be isolated by decanting the water from the oil and separating the gaseous products from the liquid products, for example in a flash drum. The ketone stream is then in step d) subjected to both hydrodeoxygenation reaction conditions and to hydroisomerisation reaction conditions.

The hydrodeoxygenation and hydroisomerisation reaction conditions may either be done simultaneously or in sequence. The product is a deoxygenated and isomerised base oil stream comprising the renewable base oil.

The hydrodeoxygenation reaction may be performed in the presence of a hydrodeoxygenation catalyst, such as CoMo, NiMo, NiW, CoNiMo on a support, for example an alumina support. The hydrodeoxygenation catalyst may be typical hydrodeoxygenation catalysts in the art, for example it may comprise a hydrogenation metal on a support, such as for example a catalyst selected from a group consisting of Pd, Pt, Ni, Co, Mo, Ru, Rh, W or any combination of these. The hydrodeoxygenation step is done under hydrodeoxygenation conditions to provide the base oil product. The hydrodeoxygenation step may for example be conducted at a temperature of 250-400° C. and at a pressure of 20-80 barg. The hydrotreatment step may for example be conducted at a temperature of 250-400° C., at a pressure of between 20 and 80 barg, a WHSV of 0.5-3 $h^{-1}$, and a $H_2$/oil ratio of 350-900 nl/l.

As mentioned above, the hydrodeoxygenation reaction conditions may comprise: a temperature in the range from 250 to 400° C.; a pressure in the range from 20 to 80 barg; a WHSV in the range from 0.5-3 $h^{-1}$; and a $H_2$ flow of 350-900 nl $H_2$/l feed. The catalyst may be NiMo on alumina support.

Preferably, the hydrodeoxygenation condition may involve a temperature in the range from 280 to 350° C.; a pressure in the range from 30 to 60 barg; a WHSV in the range from 1.0-2.5 $h^{-1}$; and a $H_2$ flow of 350-750 nl $H_2$/l feed. The catalyst may be NiMo on alumina support.

More preferably, the hydrodeoxygenation condition may involve a temperature in the range from 300 to 330° C.; a pressure in the range from 40 to 50 barg; a WHSV in the range from 1.0-2.0 $h^{-1}$; and a $H_2$ flow of 350-500 nl $H_2$/l feed. The catalyst may be NiMo on alumina support.

Further in the process, the ketone stream may be diluted with a stream of hydrocarbons. The dilution may be 30 wt % hydrocarbons and 70 wt % ketone stream, for example between 30-85 wt % hydrocarbon and 15-70 wt % ketone stream. The stream of hydrocarbons used for dilution may in part or fully be product recycle.

The product recycle may have undergone fractionation before being recycled, for example it may be the fraction boiling above 380° C. that is recycled or any other fraction of the base oil mixture described herein.

As mentioned above hydrodeoxygenation catalyst may for example be a molybdenum or wolfram catalyst, typically on a support, such as $Al_2O_3$. The catalyst may or may not be promoted. Typical promoters are Ni and/or Co. Promoted hydrodeoxygenation catalysts may for example be NiMo, CoMo, NiW, CoW, NiCoMo. When a wolfram based catalyst is used, such as a NiW, or a Pd or Pt catalyst it has the further advantage that it can also catalyse isomerisation reactions, thus enabling a simultaneous hydrodeoxygenation and hydroisomerisation reaction. Accordingly, the hydrodeoxygenation and isomerisation catalyst may be the same, such as for example NiW, or a Pt catalyst, such as Pt/SAPO in mixture with a promoted Mo catalyst on a support, e.g. NiMo on alumina.

The hydrodeoxygenation is done in the presence of hydrogen gas in a hydrodeoxygenation zone, which may be a catalyst bed in a fixed bed reactor.

When the hydrodeoxygenation and hydroisomerisation of step d) takes place in sequence, in-between the hydrodeoxygenation and hydroisomerisation there may be a stripping step, where gasses are separated from liquids. This may occur in a high temperature and high pressure separation step, for example at a temperature between 300-330° C. and pressure between 40-50 barg.

Hydroisomerisation of the Ketone Stream

The product of the hydrodeoxygenation step is subjected to an isomerization step in the presence of hydrogen and an isomerization catalyst. Both the hydrotreatment step and isomerisation step may be conducted in the same reactor, and even in the same reactor bed. The isomerisation catalyst may be a noble metal bifunctional catalyst such as a Pt containing commercial catalyst, for example Pt-SAPO or Pt-ZSM-catalyst or for example a non-noble catalyst, such as NiW. The hydrodeoxygenation and hydroisomerisation steps may be done in the same catalyst bed using e.g. the NiW catalyst in both the hydrotreatment and isomerisation step. The NiW catalyst may additionally result in more hydrocracking to diesel and naphtha products, and may be an advantageous catalyst if such products are also desired together with the renewable base oil product. The isomerization step may for example be conducted at a temperature of 250-400° C. and at a pressure of 10-60 barg. As explained elsewhere in this description, it is desirable to reduce the severity of the isomerisation reaction to avoid or reduce the amount of cracking of the renewable base oil product. The isomerisation step may for example be conducted at a temperature of 250-400° C., at a pressure of between 10 and 60 barg, a WHSV of 0.5-3 $h^{-1}$, and a $H_2$/oil ratio of 100-800 nl/l.

The hydrodeoxygenation and hydroisomerisation reactions may be done in sequence. The sequence is typically hydrodeoxygenation followed by hydroisomerisation, but this sequence may also be reversed. The isomerisation reaction conditions may comprise one or more of the following: a temperature in the range from 250 to 400° C.; a pressure in the range from 10 to 60 barg; a WHSV in the range from 0.5-3 $h^{-1}$; a $H_2$ flow of 100-800 nl $H_2$/l feed.

Preferably the isomerisation reaction conditions comprise a temperature in the range from 280 to 370° C.; a pressure in the range from 20 to 50 barg; a WHSV in the range from 0.5-2.0 $h^{-1}$; a $H_2$ flow of 200-650 nl $H_2$/l feed.

More preferably the isomerisation reaction conditions comprise a temperature in the range from 300 to 350° C.; a pressure in the range from 25 to 45 barg; a WHSV in the range from 0.5-1.0 $h^{-1}$; a $H_2$ flow of 300-500 nl $H_2$/l feed.

The hydroisomerisation reaction may be in the presence of an isomerisation catalyst, such as a catalyst comprising a Group VIII metal, preferably Pt, and a molecular sieve, optionally on support. The support may for example be selected from silica, alumina, clays, titanium oxide, boron oxide, zirconia, which can be used alone or as a mixture, preferably silica and/or alumina. The molecular sieve may for example be zeolites, such as ZSM or aluminophosphate molecular sieves, such as SAPO, such as SAPO-11, MeAPO, MeAPSO, where Me is e.g. Fe, Mg, Mn, Co or Zn, or other elements (EI) molecular sieves EIAPO or EIAPSO, e.g. silica-alumina, Y zeolite, SAPO-11, SAPO-41, ZSM-22, ferrierite, ZSM-23, ZSM-48, ZBM-30, IZM-1, COK-7. Suitable molecular sieves and characteristics of molecular sieves suitable for hydroisomerisation applications are known to the skilled person and have been described in the literature, such as in Handbook of heterogeneous catalysis from VCH Verlagsgesellschaft mbH with editiors Ertl, KnÖzinger and Weitkamp, volume 4, pages 2036-2037, which is hereby incorporated by reference herein.

Purifying the Base Oil

Between steps d) and e) of the method, there may be a stripping step, where gasses are separated from liquids. This may be done at a temperature between 320-350° C. and pressure between 3-6 barg.

Between steps d) and e) of the method, and preferably after the stripping step if present, there may also be an optional hydrofinishing step, where the product are stabilised by conducting a further hydrogenation step in the presence of a hydrogenating catalyst, for example as described above under the heading "Hydrodeoxygenation of the ketone stream", for example NiMo on an alumina support. However, other hydrofinishing catalysts containing metals of the Group VIII of the periodic system of the elements on e.g. an alumina and/or silica support may also be used. The hydrofinishing catalyst is preferably a supported Pd, Pt, or Ni catalyst, the support being alumina and/or silica.

The hydrofinishing step is similar to the prehydrogenation step with regards to the reaction conditions. However, in the hydrofinishing step, typically higher pressures, and to some extent higher temperatures are utilised. This is because the feed is fully deoxygenated at this stage compared to a potential prehydrogenation step. The hydrofinishing step is present in order to stabilise the product which among other things involves hydrogenation of double bonds or aromatic compounds that is present or has formed during the previous steps, such as during hydroisomerisation. The hydrofinishing step may be conducted at a temperature below 300° C., such as below 280° C. or below 260° C. The hydrofinishing may also be above 180° C., such as above 190° C. or above 200° C. For example the temperature for prehydrogenation may be 180-300° C., such as 190-280° C., for example 200-250° C. The pressure may be 100-200 barg, such as 120-180 barg, for example 140-160 barg. The WHSV may be 0.5-3.0 $h^{-1}$, such as 0.75-2.5 $h^{-1}$, for example 1.0-2.0 $h^{-1}$. The $H_2$/oil ratio may be 100-500 nl/l, such as 150-450 nl/l, for example 200-400 nl/l. Accordingly, the prehydrogenation may preferably be conducted at 90-300° C., 10-70 barg, WHSV of 0.5-3.0 $h^{-1}$, and $H_2$/oil ratio of 100-500 nl/l; more preferably at 110-280° C., 20-60 barg, WHSV of 1.0-2.5 $h^{-1}$, and $H_2$/oil ratio of 150-450 nl/l; even more preferably at 120-260° C., 30-50 barg, WHSV of 1.0-2.0 $h^{-1}$, and $H_2$/oil ratio of 200-400 nl/l.

The deoxygenated and isomerised base oil stream obtained in step d) comprises the renewable base oil. It may optionally in a step e) be distilled to obtain a distilled renewable base oil; for example the deoxygenated and isomerised base oil stream may be distilled to obtain the renewable base oil in a fraction having a boiling point of more than 380° C., such as more than 450° C., for example more 460° C. or more, such as 470° C. or more, such as 480° C. or more, or for example 500° C. or more. For example the distillation may yield one or more fractions of renewable base oils, for example above 380° C., for example a fraction between 380-450° C. and a fraction above 450° C.

During distillation other fractions, such as a naphtha fraction and/or a diesel fraction may also be isolated. These fractions are the result of cracking during the hydrodeoxygenation and hydroisomerisation reactions, as well as a very little amount of unconverted free fatty acid from the ketonisation step.

Hydrodeoxygenation and Isomerisation of the FFA Depleted Feed(s)

The one or more free fatty acid depleted feed(s) may be transformed into a middle distillate product, such as a diesel product, preferably in a step f) by being subjected to both hydrodeoxygenation reaction conditions and to hydroisomerisation reaction conditions, simultaneously or in sequence, to yield a deoxygenated and isomerised diesel stream comprising the diesel fuel; optionally distilling the stream obtained from step f) to obtain a distilled diesel fuel.

This may be done in the same manner as described under the heading "Hydrodeoxygenation and isomerisation of the ketone stream". The one or more free fatty acid depleted feed(s) may also be diluted with a stream of hydrocarbons before the hydrodeoxygenation and hydroisomerisation. The dilution may be 30 wt % hydrocarbons and 70 wt % stream, for example between 30-85 wt % hydrocarbon (diluent) and 15-70 wt % free fatty acid depleted feed (fresh feed). The dilution may also be high for example 3:1 and up to 20:1, for example 4:1 and up to 20:1, such as 5:1 and up to 20:1 (hydrocarbons:fresh feed) The stream of hydrocarbons used for dilution may in part or fully be product recycle.

The product recycle may have undergone fractionation before being recycled, for example it may be the fraction boiling in the diesel range of around 180-350° C., such as 210-380° C. that is recycled.

Renewable Base Oil, Diesel and Naphtha

The method according to the present invention produces renewable base oil and renewable diesel. In the course of production the renewable base oil will also comprise small amounts of renewable diesel and naphtha as explained above. The deoxygenated and isomerised diesel stream comprises in addition to the renewable diesel fuel small amounts of renewable naphtha, which can be separated and pooled with the renewable naphtha from the renewable base oil fractionation, and the renewable diesel obtained from distillation of the deoxygenated and isomerised diesel stream can be pooled with the renewable diesel from the renewable base oil fractionation.

Accordingly, the process may additionally be for producing a naphtha fuel, where the naphtha fuel is obtained from distillation of both the deoxygenated and isomerised base oil stream of step d) and from the distillation of the deoxygenated and isomerised diesel stream of step f).

For example the combined amounts of renewable naphtha, diesel and base oil obtained from the feedstock of biological origin may be between 5-95 wt % renewable base oil, 5-95 wt % diesel, and 0-30 wt % naphtha; for example between 5-95 wt % renewable base oil, 5-95 wt % diesel, and 5-30 wt % naphtha.

The Invention Will Now be Described with Reference to the Figures.

FIG. 1 describes a method for producing a renewable base oil from a feedstock of biological origin denoted "PFAD". While the feedstock of biological origin in FIG. 1 has been denoted PFAD, the method in FIG. 1 is not limited to PFAD, but may be any feedstock of biological origin as described herein.

The method comprises a step a) of providing the feedstock of biological origin as described herein, in particular under the heading "Feedstock" above. The feedstock of biological origin denoted "PFAD" is then in a step b) separated into at least a free fatty acid feed by distillation denoted "FFA distillation", where a distillate having a higher concentration of free fatty acids than the feedstock is obtained. Reference is made to the section above titled "Separation of the feedstock". The free fatty acid feed obtained from the "FFA distillation" is then in a step c) subjected to ketonisation reaction conditions (denoted "Ketonisation") where two fatty acids react to yield a ketone stream, the ketone stream comprising as the major part ketones. Reference is made to the section above titled "Ketonisation" for additional details about the ketonisation step.

The ketone stream is then in a step d) subjected to hydrodeoxygenation reaction conditions, denoted "HDO", where hydrogen is also supplied. When the hydrodeoxygenation and hydroisomerisation steps take place in sequence rather than simultaneously, the deoxygenated base oil stream may be stripped of water and gasses in a stripping step, denoted "intermediate stripper". The HDO step may be as described above under the heading "Hydrodeoxygenation of the ketone stream", and the stripping step may be as described above under the heading "Purifying the base oil". The deoxygenated base oil may then be subjected to hydroisomerisation reaction conditions, denoted "Isomerisation", where hydrogen is also supplied, yielding a deoxygenated and isomerised base oil stream comprising the renewable base oil. The hydroisomerisation conditions may be as described above under the heading "Hydroisomerisation of the ketone stream". When the hydrodeoxygenation and hydroisomerisation step takes place simultaneously, as for example as described under the heading "Hydroisomerisation of the ketone stream", then the "HDO" and "Isomerisation" are one and same reactor, and the "intermediate stripper" is placed downstream of the simultaneous hydrodeoxygenation and hydroisomerisation. The deoxygenated and isomerised base oil stream may optionally be stabilised denoted "Product stabilization", for example as disclosed above under the heading "Purifying the base oil".

The method also comprises a step e) of distilling the product of step d) to obtain a distilled renewable base oil, typically under vacuum, denoted "Vacuum distillation", for example as disclosed above under the heading "Purifying the base oil". The distillation may yield one or more fractions of renewable base oils, collectively denoted "RBO", for example above 380° C., for example a fraction between 380-450° C. and an fraction above 450° C.

By-products from the product stabilization and fractions other than the RBO fractions from the vacuum distillation may be directed as streams to fuel production denoted "Stream to fuel production", for example for the production of one or more fractions in the naphtha boiling range, such as below 180° C. and diesel boiling range, 180-350° C., for example as described above under the heading "Renewable base oil, diesel and naphtha".

FIG. 2, describes in addition to the "PFAD", "FFA distillation", "Ketonisation", "HDO", "intermediate stripper", "Isomerisation", "Product stabilization", "Vacuum distillation", and "RBO" of FIG. 1, three elements, which can be used together with the method either alone or in combination.

The first element is shared support units for base oil and diesel production ("Shared support units for baseoil and diesel production"), which may involve the removal of water formed during the ketonisation reaction and the hydrodeoxygenation by stripping or decantation (for example in the form of a sour water stripper denoted "Sour water stripper" in FIG. 3). The shared support units additionally provides for the possibility of having a recycle gas loop in order to recycle hydrogen from the hydrodeoxygenation step ("HDO") or from the diesel fuel production ("Diesel fuel production"), optionally purifying the hydrogen gas by removal of e.g. steam in a stripper before being fed to the ketonisation step ("Ketonization") as a pressurising gas for the ketonisation reaction, as for example disclosed above under the heading "Ketonisation".

The second element is the hydrofinishing step for saturation of potential aromatic compounds or double bonds present in order to stabilise the product ("Product stabilisation"), as described above under the heading "Purifying the base oil". The product stabilization will also stabilise the potential naphtha boiling range ("Naphta stabilization") and diesel boiling range ("Diesel stabilization") compounds present in the renewable base oil due to e.g. cracking during hydroisomerisation and/or from the FFA that did not react in the ketonisation reaction and was carried forward. The vacuum distillation ("Vacuum distillation") of the renewable base oil may therefore yield one or more fractions of renewable base oils, collectively denoted "RBO", for example above 380° C., for example a fraction between 380-450° C. and an fraction above 450° C., as well as one or more fractions in the Naphtha boiling range, such as below 180° C. and diesel boiling range, 180-350° C., for example as described above under the heading "Renewable base oil, diesel and naphtha".

The third element is the separation step ("FFA distillation"). The separation of the feedstock of biological origin ("PFAD") into a free fatty acid feed, which is processed into renewable base oil ("RBO") via ketonisation, and a bottom stream ("Bottom stream"), which can for example be further processed into a diesel fuel ("Diesel fuel production"). The separation step ("FFA distillation") allows for a more versatile production of renewable base oil ("RBO"), both in respect of quality of the RBO, as well as the quantity. With regards to the quality, the FFA distillation can, as shown in example 1, produce a free fatty acid feed essentially consisting only of e.g. palmitic acid. This single carbon fatty acid can then be processed via ketonisation to renewable base oil which consists essentially of $C_{31}$ base oil having a well-defined composition, which is an industrially relevant product for base oil producers in that they are able to fine tune the particular properties required of base oils.

With regards to the quantity, the separation step also provides for an RBO production that can be scaled depending on the demand of the market for either renewable base oil or renewable diesel; if more diesel is demanded than base oil, the separation step can for example take a more narrow cut of exclusively palmitic acid and produce a base oil with a very well-defined composition, whereas if less renewable diesel is demanded by the market, the separation step can for example take a more broad cut of the feedstock of biological origin, which may for example include both the $C_{16}$ and $C_{18}$ fatty acids, which can be processed into renewable base oil products via ketonisation, yielding RBO mixtures comprising $C_{31}$, $C_{33}$ and $C_{35}$ base oils. The amount of free fatty acids in a feedstock of biological origin as defined herein (see e.g. the section titled "feedstock") may be further increased by prior to step a) of the method, the initial feedstock comprising fatty acid esters may be pre-treated in at least a hydrolysis step thereby producing the feedstock, where the ratio of free fatty acids to fatty acid esters has been increased compared to the initial feedstock.

FIG. 3, describes in addition to FIGS. 1 and 2 that the bottom stream of FIG. 2 is now a fatty acid depleted feed ("renewable diesel line") for the production of diesel in a step f) of subjecting the one or more free fatty acid depleted feed(s) ("renewable diesel line") to an optional prehydrogenation stage ("pretreatment") conducted under mild conditions in the presence of a hydrogenation catalyst, as described under the heading "Ketonisation". The prehydrogenation is intended to saturate double bonds in the remaining fatty acids and fatty acid esters, which enables the use of more severe hydrodeoxygenation conditions in the subsequent step ("HDO").

The HDO step may be as described above under the heading "Hydrodeoxygenation and isomerisation of the FFA depleted feed(s)". The water is separated ("Sour water stripper") in a stripper, which may be shared with the RBO line. Additionally, hydrogen may be recycled via the recycle gas loop, which may also be shared with the RBO line. The deoxygenated diesel stream may then be subjected to hydroisomerisation reaction conditions, denoted "Isomerisation", where hydrogen is also supplied, yielding a deoxygenated and isomerised diesel stream comprising the diesel fuel.

As mentioned above under the section "Hydrodeoxygenation and isomerisation of the FFA depleted feed(s)", the hydrodeoxygenation and hydroisomerisation may be conducted simultaneously or in sequence. The deoxygenated and isomerised diesel stream may optionally be stabilised denoted "Diesel stabilization" and "Naphta stabilization", for example in the form of the hydrofinishing step as disclosed above under the heading "Purifying the base oil". The vacuum distillation ("Vacuum distillation") of the a deoxygenated and isomerised diesel stream may therefore yield one or more fractions of Diesel fuel, collectively denoted "Diesel", in e.g. the boiling range, 180-350° C., as well as one or more fractions in the Naphtha boiling range, such as below 180° C., for example as described above under the heading "Renewable base oil, diesel and naphtha".

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The terms "comprising", "comprise" and comprises herein are intended by the inventors to be optionally substitutable with the terms "consisting of", "consist of" and "consists of", respectively, in every instance.

EXAMPLES

Example 1—Separation of PFAD into a Palmitic Acid Feed and a Palmitic Acid Depleted Feed Palm fatty acid distillate (PFAD) was separated into a palmitic acid feed and a palmitic acid depleted feed by distillation at a temperature of about 250-275° C. and at 0.01-0.05 bar pressure.

This resulted in a palmitic acid feed, which was 97.0 wt % pure with minor impurities of: $C_{18}$ fatty acids (0.42 wt %); $C_{14}$ fatty acids (2.5 wt %).

The remaining palmitic acid depleted feed contained partial glycerides and $C_{18}$ fatty acids as the primary components:

TABLE 1

Distillation of PFAD

| Carbon number | PFAD feed (wt %) | Distillate (wt %) (Enriched feed) | Bottom (wt %) (depleted feed) |
|---|---|---|---|
| C14:0 FFA | 1.1 | 2.5 | 0.0 |
| C16:0 FFA | 42.4 | 97 | 0.4 |
| C18:2 FFA | 1.2 | 0.2 | 2.0 |

TABLE 1-continued

Distillation of PFAD

| Carbon number | PFAD feed (wt %) | Distillate (wt %) (Enriched feed) | Bottom (wt %) (depleted feed) |
|---|---|---|---|
| C18:1 FFA | 42.1 | 0.2 | 74.4 |
| C18:0 FFA | 4.5 | 0.01 | 8.0 |
| MG | 0 | 0 | 0.0 |
| DG | 2.6 | 0 | 4.6 |
| TG | 6.1 | 0 | 10.8 |

FFA: free fatty acids; MG, DG, TG: mono-, di-, tri-glyderides

Example 2—Ketonisation of the Palmitic Acid Feed

The palmitic acid feed was fed to a fixed bed (pilot) reactor operated in continuous mode comprising a catalyst bed loaded with 250 g catalyst material ($TiO_2$ BET 50-54 $m^2/g$; average pore size 100-200 Å; crystallinity 50-100%). The ketonisation was conducted in the liquid phase at a pressure of about 18 barg, temperature of about 360° C., WHSV of about 1.0 $h^{-1}$, and an extra gas flow of 131 l/h nitrogen. The ketonisation reaction conditions resulted in 85% fatty acid conversion thereby obtaining a ketone stream.

Example 2a—Ketonisation of the Palmitic Acid Feed

The palmitic acid feed was fed to a fixed bed reactor operated in continuous mode comprising a catalyst bed loaded with 250 g catalyst material ($TiO_2$ BET 50-54 $m^2/g$; average pore size 100-200 Å; crystallinity 50-100%). The ketonisation was conducted in the liquid phase at a pressure of about 25 barg, temperature of about 360° C., WHSV of about 0.5 $h^{-1}$, without extra gas flow. The ketonisation reaction conditions resulted in 99.9% fatty acid conversion thereby obtaining a ketone stream.

Example 2b—Ketonisation of the Palmitic Acid Feed

The palmitic acid feed was fed to a fixed bed reactor operated in continuous mode comprising a catalyst bed loaded with 20 g catalyst material ($TiO_2$ BET 50-54 $m^2/g$; average pore size 100-200 Å; crystallinity 50-100%). The ketonisation was conducted in the liquid phase at a pressure of about 10 barg, temperature of about 360° C., WHSV of about 1.0 $h^{-1}$, and an extra gas flow of 5 l/h hydrogen. The ketonisation reaction conditions resulted in 99.9% fatty acid conversion thereby obtaining a ketone stream.

Example 2c—Ketonisation of the Palmitic Acid Feed

The palmitic acid feed was fed to a fixed bed reactor operated in continuous mode comprising a catalyst bed loaded with 20 g catalyst material ($TiO_2$ BET 50-54 $m^2/g$; average pore size 100-200 Å; crystallinity 50-100%). The ketonisation was conducted in the liquid phase at a pressure of about 10 barg, temperature of about 360° C., WHSV of about 1.0 $h^{-1}$, and an extra gas flow of 5 l/h carbon dioxide. The ketonisation reaction conditions resulted in 99.4% fatty acid conversion thereby obtaining a ketone stream.

Example 3—Hydrodeoxygenation and Isomerisation of the Ketone Stream

The resulting ketone stream was hydrodeoxygenated over a $NiMo/Al_2O_3$ catalyst at a temperature of about 310° C., a pressure of about 40 bar, a WHSV of about 1.5 $h^{-1}$, and $H_2$/feed oil ratio of 900 nl/l to yield a hydrodeoxygenated product. The efficiency of oxygen removal was 99.9% for the HDO step.

The resulting hydrodeoxygenated product was hydroisomerised over Pt/SAPO-11 on alumina support as the hydroisomerisation catalyst with at a temperature of about 350° C., a pressure of about 40 bar, and at a WHSV of about 1.0 $h^{-1}$ to yield hydroisomerised base oil product.

The hydroisomerised base oil product is fractionated into a naphtha fraction (below 180° C.), a diesel fraction (180-350° C.), and the 380+° C. fraction was isolated as a renewable base oil product.

Example 3a—Hydrodeoxygenation and Isomerisation of the Ketone Stream

The resulting ketone stream was hydrodeoxygenated over a $NiMo/Al_2O_3$ catalyst at a temperature of about 310° C., a pressure of about 40-50 bar, a WHSV of about 1.5 $h^{-1}$, and $H_2$/feed oil ratio of 900 nl/l to yield a hydrodeoxygenated product. The efficiency of oxygen removal was 99.9% for the HDO step.

The resulting hydrodeoxygenated product was hydroisomerised over Pt/SAPO-11 on alumina support as the hydroisomerisation catalyst with a temperature of about 348° C., a pressure of about 40 bar, at a WHSV of about 1.0 $h^{-1}$, and $H_2$/feed oil ratio of 800 nl/l oil to yield a hydroisomerised base oil product.

The hydroisomerised base oil product is fractionated into a naphtha fraction (below 180° C.), a diesel fraction (180-350° C.), and the 380+° C. fraction was isolated as a renewable base oil product (59.9 wt %), renewable diesel (22.9 wt %), renewable naphtha boiling in the range of 35-180° C. (1.3 wt %) the remainder being product gasses (11.9 wt %) and process oil boiling between 350-380° C. (4.0 wt %).

The renewable base oil product had the following properties: Kinematic viscosity at 40° C. of 17.7 $mm^2/s$; Kinematic viscosity at 100° C. of 4.2 $mm^2/s$; a viscosity index (VI) of 151; cloud point of −1.1° C.; pour point of −17° C.; and aromatics content below 0.1 wt %. The kinematic viscosities measured using ENISO3104, Viscosity index using ASTM D 2270; cloud point using ASTM D 5771; and pour point using ASTM D 5950; aromatic compounds using ASTM D 7419.

Example 4—Hydrodeoxygenation and Isomerisation of the Remaining Palmitic Acid Depleted Stream The remaining palmitic acid depleted feed was hydrodeoxygenated over a $NiMo/Al_2O_3$ catalyst at a temperature of about 310° C., a pressure of about 50 bar, a WHSV of about 1.0-1.5 $h^{-1}$, and $H_2$/feed oil ratio of 900 nl/l to yield a hydrodeoxygenated product. The efficiency of oxygen removal was 99.9% for the HDO step.

The resulting hydrodeoxygenated product was hydroisomerised over a reduced platinum molecular sieve/$Al_2O_3$ as the hydroisomerisation catalyst with at temperatures of about 300-350° C., a pressure of about 20-40 bar, and at a WHSV of about 0.8-1.0 h$^{-1}$ to yield a hydroisomerised base oil product.

The hydroisomerised diesel product is fractionated into a naphtha fraction (below 180° C.), a diesel fraction (180-350° C.).

The invention claimed is:

1. A method for producing a renewable base oil and a diesel fuel from a feedstock of biological origin, the method comprising:
   a) providing a feedstock, the feedstock containing 2-95 wt % of a mixture of free fatty acids; 5-98 wt % fatty acid glycerols selected from mono-glycerides, di-glycerides and tri-glycerides of fatty acids; and 0-50 wt % of one or more compounds selected from a list consisting of: fatty acid esters of the non-glycerol compound, fatty amides, and fatty alcohols; wherein at least 50 wt % of the feedstock is made up of the mixture of free fatty acids and fatty acid glycerols;
   b) separating the feedstock into at least:
      a free fatty acid feed having a higher concentration of free fatty acids than the feedstock, the free fatty acids containing $C_{10}$-$C_{24}$ fatty acids; and
      one or more free fatty acid depleted feed(s) having higher concentration of the compounds selected from mono-glycerides, di-glycerides and tri-glycerides of fatty acids, and having a higher boiling point than the free fatty acid feed;
   c) subjecting the free fatty acid feed to ketonisation reaction conditions where two fatty acids react to yield a ketone stream, the ketone stream containing as a major part saturated ketones;
   d) subjecting the ketone stream to both hydrodeoxygenation reaction conditions and to hydroisomerisation reaction conditions, simultaneously or in sequence, to yield a deoxygenated and isomerised base oil stream containing the renewable base oil; and
   e) transforming the one or more free fatty acid depleted feed(s) into a diesel fuel.

2. The method according to claim 1, comprising:
   prior to step a), pre-treating an initial feedstock containing fatty acid esters in at least a hydrolysis step thereby producing the feedstock, where a ratio of free fatty acids to fatty acid esters has been increased compared to the initial feedstock.

3. The method according to claim 1, wherein the free fatty acid feed contains $C_{14}$-$C_{22}$ fatty acids.

4. The method according to claim 1, comprising:
   distilling the deoxygenated and isomerised base oil stream of step d) to obtain a distilled renewable base oil.

5. The method according to claim 1, comprising:
   f) where the one or more free fatty acid depleted feed(s) is transformed into a diesel product by subjecting the one or more free fatty acid depleted feed(s) to both hydrodeoxygenation reaction conditions and to hydroisomerisation reaction conditions, simultaneously or in sequence, to yield a deoxygenated and isomerised diesel stream containing the diesel fuel; and
   distilling the deoxygenated and isomerised diesel stream obtained from step f) to obtain a distilled diesel fuel.

6. The method according to claim 4, comprising:
   f) where the one or more free fatty acid depleted feed(s) is transformed into a diesel product by subjecting the one or more free fatty acid depleted feed(s) to both hydrodeoxygenation reaction conditions and to hydroisomerisation reaction conditions, simultaneously or in sequence, to yield a deoxygenated and isomerised diesel stream containing the diesel fuel; and
   g) distilling the deoxygenated and isomerised diesel stream obtained from step f) to obtain a distilled diesel fuel.

7. The method according to claim 6, additionally for producing a naphtha fuel, where the naphtha fuel is obtained from distillation of both the deoxygenated and isomerised base oil stream of step d) and from the distillation of a deoxygenated and isomerised diesel fuel of step e).

8. The method according to claim 6, wherein no pre-treatment by hydrogenation or by hydrolysis is made in or in-between steps a)-c).

9. The method according to claim 6, where the hydrodeoxygenation and hydroisomerisation of step d) take place in sequence, and where in-between the hydrodeoxygenation and hydroisomerisation there is a stripping step, where gasses are separated from liquids in a high temperature and high pressure separation step at a temperature between 300-330° C. and pressure between 40-50 barg.

10. The method according claim 6, wherein between steps d) and e) there is a stripping step, where gasses are separated from liquids, at a temperature between 320-350° C. and pressure between 3-6 barg.

11. The method according to claim 6, wherein the free fatty acid feed contains more than 90 wt % saturated fatty acid or $C_{16}$ fatty acids.

12. The method according to claim 6, wherein the feedstock is palm oil fatty acid distillate (PFAD).

13. The method according to claim 6, wherein the ketonisation reaction conditions include a temperature in a range from 300 to 400° C., a pressure in a range from 5 to 30 barg and a WHSV in a range from 0.25-3 h$^{-1}$, in a presence of a ketonisation catalyst, the ketonisation catalyst containing a metal oxide catalyst, in a presence of a gas in a range from 0.1-1.5 gas/feed ratio (w/w), the gas being selected from one or more of: $CO_2$, $H_2$, $N_2$, $CH_4$, and $H_2O$.

14. The method according to claim 6, wherein the ketonisation reaction conditions ensure liquid phase ketonisation; wherein the ketonisation catalyst is a metal oxide catalyst selected from a list to contain metal consisting of one or more of: Ti, Mn, Mg, Ca, and Zr.

15. The method according to claim 6, wherein the ketonisation catalyst is $TiO_2$ in anatase form having an average pore diameter of 80-160 Å, and/or a BET area of 40-140 m$^2$/g, and/or porosity of 0.1-0.3 cm$^3$/g.

16. The method according to claim 14, wherein the ketonisation catalyst is $TiO_2$, on a support, wherein a content of elements manganese, magnesium, calcium and potassium, are 0.05 wt % or less compared to a total catalyst weight as measured using X-ray diffraction.

17. The method according to claim 14, wherein the ketonisation catalyst is $TiO_2$ on a support, wherein a content of the element potassium, is 0.05 wt % or less compared to a total catalyst weight as measured using X-ray diffraction.

18. The method according to claim 14, wherein the hydrodeoxygenation reaction conditions of step d) and/or step f) include a temperature in a range from 250 to 400° C., a pressure in a range from 20 to 80 barg, a WHSV in a range from 0.5-3 h$^{-1}$, and a $H_2$ flow of 350-900 nl $H_2$/l feed, in a presence of a hydrodeoxygenation catalyst NiMo on an alumina support.

19. The method according to claim 6, wherein the hydroisomerization reaction conditions of step d) and/or step f) include a temperature in a range from 250 to 400° C., a pressure in a range from 10 to 60 barg, a WHSV in a range from 0.5-3 h$^{-1}$, and a $H_2$ flow of 100-800 nl $H_2$/l feed, in a presence of an isomerisation catalyst including a Group VIII metal and a molecular sieve, on an alumina and/or silica support.

20. The method according to claim 6, wherein the hydrodeoxygenation catalyst and isomerisation catalyst are the same; and
   wherein more than 50 wt % of the feedstock is the mixture of free fatty acids and fatty acid glycerols.

21. The method according to claim 6, wherein the feedstock comprises:
   at least 10 wt % and below 90 wt % free fatty acids.

22. The method according to claim 6, wherein the feedstock comprises:
   at least 10 wt % and below 90 wt % fatty acid esters.

23. The method according to claim 6, wherein the feedstock comprises:
   at least 10 wt % and below 90 wt % free fatty acids and at least 10 wt % and below 90 wt % fatty acid esters, and wherein more than 70 wt % of the feedstock is said mixture of free fatty acids and fatty acid glycerols.

24. The method according to claim 6, wherein said fatty acid esters are fatty acid glycerols.

* * * * *